United States Patent Office

Plant Pat. 1,449
Patented Jan. 17, 1956

1,449

PEACH TREE

David Bates Perrine, Centralia, Ill.

No Drawing. Application October 18, 1954, Serial No. 463,077

1 Claim. (Cl. 47—62)

This invention relates to a new and distinct variety of peach tree and more particularly to a mutation of the non-patented variety "Redhaven" peach.

This new variety has much the same growing habits and other characteristics of both the tree and fruit as the parent variety but distinctly differs therefrom primarily in the ripening of the fruit of the new variety about a full week later than the fruit of the non-patented variety "Redhaven," when grown under comparable conditions. The new variety grows larger and somewhat rounder than the parent variety with the fruit quality being almost identical except for a somewhat snappier flavor of the mutation. The new variety of peach tree herein described was originated and successfully asexually propagated in the following manner:

In the fall of 1941, approximately 650 trees of the "Redhaven" peach were purchased from 2 nurseries and planted in the spring of 1942 in an orchard at Centralia, Illinois. When this orchard began fruiting, it was noted that one tree was later in ripening its crop than the others. Continued observation indicated that it was not merely a "Redhaven" which was maturing late, but a distinct mutation of that variety. This assumption was proved to be a fact by asexual reproduction, with 2 generations having retained the identifying characteristics of the parent tree.

Asexual reproduction of the new variety, by scion grafting and budding, was conducted near the city of Centralia, Marion County, Illinois.

Referring now more specifically to the pomological details of this new and distinct variety of peach tree, the following is a description thereof:

*Tree*

In general, the tree is so nearly like the "Redhaven" as to be indistinguishable, being a sturdy grower of good size with the limbs coming off the main stem at blunt angles, giving the tree good structural form and strength. The wood is exceptionally hardy having withstood a temperature of minus 22° F. and appears to have good hardiness and resistance to disease and insects. The tree is also naturally a heavy bearer and must be thinned early in the season to produce the large size fruit of which it is capable.

The leaves are good size, 5.5 inches long and 1.25 inches wide with the average vigor. The foliage is abundant and of an olive green color with the leaf glands being reniform. While not completely immune to *Bacterium pruni*, the foliage is not particularly susceptible.

*Flowers*

As is the case with the tree itself, the flowers of the present mutation are so nearly like the non-patented variety "Redhaven" as to be indistinguishable, being small, red type, and open at about an average time for peach bloom. Pollen is viable and ample and the flowers withstand cold and frost well. The bud formation is quite heavy and very hardy having withstood a temperature of minus 22° F., and produced ¼ of a crop the following summer.

*Fruit*

The fruit is almost spherical, without prominent suture or apex when matured. Color is a deep, rich red over a warm, creamy yellow background with the mature fruit coloring from 75–95 per cent red color. The size of the fruit depends upon the thinning practiced, and with moderate thinning gives a fruit of about 2⅜ inches, while heavy thinning produces a 3-inch or larger size.

The skin is smooth, almost fuzzless, and tough while the flesh is bright yellow, firm, and juicy. It has a small, bright red touch immediately adjoining the pit and the texture is smooth with the flesh breaking away from the pit in a normal "freestone" manner. The pits themselves are small.

The first fruits ripen about 1 week later than non-patented variety "Redhaven" or about 3 weeks before non-patented variety "Elberta" with the fruits hanging on the tree well and staying firm over a long period of time. The last picking is normally about a week before non-patented variety "Elberta." The flavor of the present mutation is spicy and vinous, with the meat resisting browning when exposed to the air. It is excellent either fresh, canned or frozen and even if picked "hard ripe," it has a good eating quality. The fruit is of average resistance to insect attack and in this respect it is similar to "Redhaven," a non-patented variety, now grown commercially in the United States.

In general, it can be said that the tree, foliage, and flowers are so nearly like "Redhaven" as to be indistinguishable. The color and general appearance of the fruits are similar, but the mutation ripens a full week later, grows larger and rounder, stays firmer (on or off of the tree), and the fruit quality is almost identical except that the mutation has a slightly snappier flavor. It will follow the "Redhaven" in maturity thus filling the gap to the early ripening strains of "Elberta" with a peach of unsurpassed appearance and quality.

Having thus described my invention, what is claimed as new and desired to be secured by Letters Patent is:

A new and distinct variety of peach tree, substantially as described, bearing large, firm, and highly colored fruit; characterized as to novelty to the "Redhaven" peach in that the color and general appearance of the fruits are similar, but the present mutation ripens a full week later, grows larger and rounder and stays firmer, with a slightly "snappier" flavor.

No references cited.